United States Patent [19]

Toyotama

[11] Patent Number: 4,913,865
[45] Date of Patent: Apr. 3, 1990

[54] PROCESS FOR PREPARING ULTRAFINE PARTICLES OF ORGANIC COMPOUNDS

[75] Inventor: Hideki Toyotama, Saitama, Japan

[73] Assignees: Research Development Corp of Japan; Stanley Electric Co. Ltd., both of Tokyo, Japan

[21] Appl. No.: 865,801

[22] Filed: May 22, 1986

[30] Foreign Application Priority Data

Jul. 15, 1985 [JP] Japan .................. 60-155375

[51] Int. Cl.$^4$ .............................. B29B 9/00
[52] U.S. Cl. .......................... 264/81; 264/5; 427/2; 427/180; 427/255.6
[58] Field of Search ............... 264/81, 5; 427/2, 180, 427/255.6

[56] References Cited

U.S. PATENT DOCUMENTS

| 3,663,265 | 5/1972 | Lee et al. ........... 427/255.6 X |
| 4,395,440 | 7/1983 | Abe et al. ............... 427/180 |
| 4,543,275 | 9/1985 | Akashi et al. ........... 427/250 |
| 4,582,731 | 4/1986 | Smith ................. 427/421 |
| 4,654,229 | 3/1987 | Morita et al. .......... 427/180 |
| 4,724,106 | 2/1988 | Morimoto et al. ........ 264/24 |

FOREIGN PATENT DOCUMENTS 1298453 12/1972 United Kingdom ............. 427/255.6

Primary Examiner—Jan H. Silbaugh
Assistant Examiner—Mary Lynn Fertig
Attorney, Agent, or Firm—Kerkam, Stowell, Kondracki & Clarke

[57] ABSTRACT

A method for manufacturing ultrafine particles of hardly water-soluble or water-insoluble organic compounds is disclosed herein, and the method includes heating and evaporating the organic compound in a vacuum vessel in which an inert gas is introduced in a desired pressure, then condensing and depositing the vaporized organic compound on a recovering means cooled, the resulting ultrafine particles exhibiting a high negative zeta potential sufficient to form a stable water dispersion thereof.

5 Claims, 3 Drawing Sheets

PROCESS FOR PREPARING ULTRAFINE PARTICLES OF ORGANIC COMPOUNDS

BACKGROUND OF THE INVENTION

1. Field of the Invention

The present invention relates to a method of the preparation of ultrafine particles of water-insoluble or hardly water soluble organic compounds and stable water dispersion thereof.

2. Description of the Prior Art

When various kinds of materials such as metals, ceramics are pulverized into fine particles (or powder), it is observed that many discrete planes are formed and the interface (or more precisely specific surface) of the material is substantially increased. Moreover, many defects are formed in the crystalline structure thereof and are chemically activated, because of their small diameter. As a result, these materials in the form of fine particles exhibit a lot of interesting properties such as high adsorptivity, high hygroscopicity, as well as catalytic activity. Thus, processes, in which powder materials are used, are frequently applied in many field such as chemical industries, medicines, insecticide or pesticide, foods, refinery, ceramics or the like.

These powders may be prepared according to various kinds of methods, for example, evaporation-condensation process, sputtering process, vapour deposition technique such as thermal decomposition or photolysis of metal halides or organometallic compounds, precipitation reaction in an aqueous solution, electrolytic process, hydronic discharge technique, spray drying method as well as mechanical pulverization and grain boundary corrosion technique or the like.

While, so-called ultrafine particles having a diameter of an order of approximately microns or angstroms have drawn attention in particular in the field of inorganic materials. The ultrafine particles of inorganic materials present excellent physical and chemical properties and are expected to apply as magnetic materials, material for powder metallurgy, chemical catalyst, light or electromagnetic wave absorber, semiconductor materials. Under these circumstances, various methods for manufacturing such ultrafine powder have been proposed and put into practical use. An example of such method comprises evaporating a material in a rare gas atmosphere while heating and condensing the resulting vapour of the material in the rare gas atmosphere to form ultrafine particles (this method is referred to as evaporation in gas atmosphere technique). Other methods, in which electric resistance element, plasma jet, induction infrared laser or plasma arc discharge is used, are also known in the art.

BRIEF DESCRIPTION OF THE INVENTION

As seen from the above description, powder materials have been used in the various kinds of fields since they exhibit a lot of interesting physical and chemical properties. However, up to now there has been proposed and reported only the ultrafine particles of metals, metal oxides and other metal compounds such as carbides, nitrides.

The powdered organic compounds are also important in certain fields, for instance, in medicines or the like. When a water-insoluble or a hardly water-soluble organic materials are used in the form of suspension or shake mixture, the improvement in stability of them is an important problem to be solved, although these water-insoluble medicines can be used in the form of powder, tablets without any problems. Therefore, development of a stable medium for such water-insoluble or a hardly water-soluble medicine becomes quite important when dealing with diseases which require an immediate effect of medicines.

For example, the injectable medicines are, in general, used in the form of aqueous solutions or dispersions which usually show an immediate effect. When the medicine is hardly soluble in water, the application thereof is, however, limited to tablets and powder and they cannot be applied in the form of a solution or suspension for injection having immediate effect, such as stable dispersion (suspension).

However, if the diameter of the water-insoluble medicines is extremely reduced by a suitable method up to the order of about microns or angstroms, it may be expected that these medicines become water-soluble or more precisely water-dispersible and as a result, they seem to be used or handled in the same manner as in the case of water-soluble one.

A solution for injection is generally administered intramucously or subcutaneously and is expected to provide an immediate effect.

Thus, a principal purpose of this invention is to provide a method for preparing ultrafine particles of hardly water-soluble or water-insoluble organic materials.

Another purpose of this invention is to provide a stable dispersion of water-insoluble or hardly water-soluble organic compounds, in particular, medicines.

A further object of this invention is to provide a method for preparing such stable dispersion of water-insoluble organic materials, in particular, medicines.

These and other purposes of this invention can be accomplished by providing a method for preparing ultrafine particles of different organic compounds, which comprises heating and evaporating an organic compound in a vacuum vessel under a desired pressure of an inert gas, condensing or depositing the resuting vapour of the compound on a recovering plate.

BRIEF DESCRIPTION OF THE ATTACHED DRAWINGS

The method according to the present invention is now explained in more detail with reference to the accompanying drawings in which.

DETAILED EXPLANATION OF THE INVENTION

Figure 1:
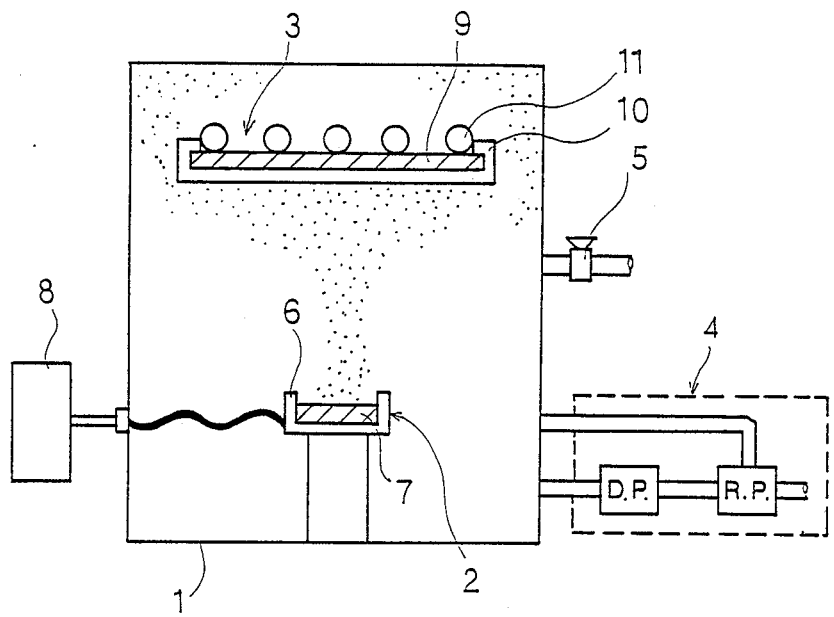
FIG. 1 is an illustrative diagram showing an apparatus for carrying out the method of this invention to form ultrafine particles of organic compounds.

The medicines are, in general, applied in various kinds of forms such as tablets, powder, swallowable injectable suspension, emulsion or sultion. Among these, injectable suspension, emulsion or solution is expected to have an immediate effect. When one intends to use medicines as the injectable forms, the medicine should be soluble in water or other mediums. Thus, it is necessary to change the chemical structure, acidity or alkalinity of the medicine, to add a surfactant, auxiliary stabilizer and/or a auxiliary solubilization agent when one want to obtain a solution or stable suspension of water-insoluble or hardly water-soluble medicines. These procedures may be quite complicated and in some cases such treatment may possibly change the effectiveness of the medicines and their toxicity (or safety). In addition, the stabilizer, auxiliary solubilizing agent should be selected from such additives which are not toxic to patients or harmful to the effectivenes of the medicine in their dose and therefore, it is necessary to pay careful attention to the selection or purity of such materials. Thus, under these circumstances it is most desirable to develop a technique for obtaining a stable dispersion of water-insoluble or hardly water-soluble medicines without using additives such as stabilizer of dispersion, auxiliary solubilizing agent or surfactant (except for the stabilizer or medicines per se).

According to the method of this invention, ultrafine particles of the following organic materials which allow us to obtain a stable water dispersion can be provided: (i) low molecular weight organic compounds, such as pyrene, anthracene, merocyanine, ferrocene, metal phthalocyanine such as copper phthalocyanine, carbazole (ii) high molecular weight organic compounds such as polyvinylchloride, polyvinylalcohol, polyethylene, polystyrene, polyvinylpyrrolidone, polyvinylcarbazole, polyethyleneterephthalate, polyvinylidenechloride, polymethylmethacrylate; (iii) water-insoluble or hardly water-soluble medicines, for example, analgesic, sedative or antiepilepsy such as α-bromoisovaleroylurea (III) (derivative of acetyluea), barbital (5,5-diethylbarbituric acid), phenobarbital (5-ethyl-5-phenylbarbituric acid), phenobarbital sodium (derivatives of barbituric acid), phenytoin (diphenylhydantoin:derivatives of hydantoin), carbamazepine (5H-dibenz[b,f]azepine-5-carboxamide:derivatives of dibenzazepine); tranquilizer such as haloperidol (4-[4-(p-chlorophenyl)-4-hydroxypiperidino]-4′-fluorobutyrophenone: butyrophenone derivatives), diazepam (7-chloro-1,3-dihydro-1-methyl-5-phenyl-2H-1,4-benzodiazepine-2-one:benzodiazepine derivatives), chlormezanone (2-[p-chlorophenyl]-tetrahydro-3-methyl-2H-1,3-thiazin-4-one-1,1-dioxine); antipyretic analgesic agents such as phenacetin, acetaminophene (aniline derivatives), aspirin (acetylsalicylic acid), ethenzamide (o-ethoxybenzamide) derivatives of acetylsalicylic acid); steroid anti-inflammatory agents such as phenylbutazone (4-butyl-1,2-diphenyl-3,5-pyrazolidine dione), indomethacin (1-[4-chlorobenzoyl]-5-methoxy-2-methyl-1H-indole-3-acetic acid), mepirizole (1-[4-methoxy-6-methyl-2-pyrimidinyl]-3-methyl-5-methoxypyrazole), probenecid (p-dipropylsulfamoyl-benzoic acid); local anesthetics such as lidocaine (2-[diethylamino]-N-2,6-[dimethylphenyl]-acetamide); sympathomimetic agents such as epinephrine (adrenaline); antihistamic agents such as cyproheptadine hydrochloride (4-(5H-dibenzo[a,d]cyclohepten-5-ylidine)-1-methylpiperidine hydrochloride); cardiotonic agents such as digitoxin (steroid cardiac glycoside); antibacterial agents such as heterocyclic sulfamines, for instance, sulfamonomethoxine (N′-[6-methoxy-4-pyrimidyl]sulfamine); oral antidiabetics such as tolubutamide (1-butyl-3-[p-tolylsulfonyl]urea); antibiotics such as chloramphenicol; disinfectant such as ethyl p-hydroxybenzoate; vitamins such as vitamin $B_{13}$ (orotic acid); steroid hormones such as cortisone acetate, predonisone (adrenocortical hormone). However, these examples are simply illustrative materials and the invention is not restricted to these examples clearly disclosed herein. The medicines listed above have a quite low watersolubiity or water-insolubility and thus it is desired to improve their affinity with respect to water so as to simplify the procedure of granulation and the procedures for obtaining stable water dispersion without using additives such as stabilizer, solubilization agents.

This can surely be attained by reducing the diameter thereof according to the process of this invention.

The method for preparing ultrafine particles of organic compounds according to the present invention may, for example, be carried out utilizing an apparatus shown in FIG. 1. The apparatus is similar to that used for manufacturing metallic ultrafine particles according to the method referred to as evaporation in gas atmosphere technique and mainly comprises a vacuum vessel 1, a heating means 2, which is disposed in the vessel 1 at its lower portion and contains starting materials, to heat and evaporate the starting material and a means 3 for recovering ultrafine particles produced. The vacuum vessel 1 is further provided with a system 4 for evacuating the vessel 1 such as oil diffusion pump, sorption pump (or the combination of one of them with liquid nitrogen trap or titanium sublimation pump) and a system 5 for introducing inert gas such as argon or helium into the vessel 1.

The heating means 2 is further composed of a container 6 for starting material 7 and a heater embedded in the wall of the container 6 and connected to power supply 8. While the recovering means 3 comprises a recovering plate 9 (for example, copper plate) covered with glass plate or aluminum foil sheet 10 and a series of cooling pipes 11 contact with the recovering plate 9. In the cooling pipe, a coolant such as water, liquid nitrogen is recycled.

When ultrafine particles of organic compounds are manufactured utilizing the apparatus shown in FIG. 1, an organic compound 7 to be formed into ultrafine particles is charged into the container 6 and the vessel 1 is evacuated to a desired degree of vacuum by the evacuation system 4. Then, an inert gas such as He, Ar is introduced into the vessel 1 through the system 5 to a desired pressure and thereafter, the heating means 2 is started to commence heating the starting material 7. The starting material 7 is thus heated and evaporated. The gas molecules of the starting material evaporated is scattered by the inert gas molecules contained in the vessel 1 to form ultrafine particles of the organic compound 7 due to the collision with the inert gas molecules. The ultrafine particles thus formed are condensed and deposited on the aluminum foil sheet 10 of the recovering means 3, which is cooled through the cooling pipes 11.

In general, the size of the particles formed according to the method of the invention depends on the pressure in the vessel 1. Therefore, ultrafine particles of a desired diameter may be obtained by adjusting the pressure of the inert gas in the vessel 1. It is also quite effective to preliminary determine the relationship between the strength of pressure and the size of ultrafine particles formed and to prepare a calibration curve when carrying out the method of this invention.

As a rule, the size of the ultrafine particles formed according to the present invention varies within a range of from 500 Å to 4 μm in proportion to the strength of inert gas pressure which is, in general, adjusted to a range of from 0.01 Torr to 10 Torr. More precisely, the size of particles formed has a tendency to decrease as the pressure in the vessel decrease. Thus, there is no limitation in the strengh of the pressure used and it may be selected depending on objects and manner of application of particles obtained.

Thus, the method of this invention may be effectively applied to all the organic materials inclusive of high molecular weight molecules having a desired level of vapour pressure to form ultrafine powder thereof. Moreover, ultrafine powder of different size may be manufactured by suitably adjusting the inert gas pressure in the vacuum vessel during the manufacturing procedures.

The resulting ultrafine powder of organic compounds may easily be dispersed in a medium such as, in particular, water and provide a quite stable dispersion, since they have a substantially improved affinity to water, a high surface energy which causes an intermolecular interaction different from those in the crystalline state. These improved properties further permit the manufacture of other interesting materials such as organic sensors (including pH sensor or the like), organic semiconductors, organic catalysts, adsorbents having good selectivity.

First of all, when the method is applied to manufacture ultrafine particles of medicines which are water-insoluble or hardly water-soluble, a stable water dispersion can surely be obtained without further treatment such as the addition of stabilizers, auxiliary solubilizing agents and/or surfactants. The preparation of such stable water dispersion has conventionally been considered to be quite difficult to form, unless the additives such as mentioned above are used together with the effective powder components obtained according to any one of conventional processes such as mechanical pulverization. Thus, the ultrafine powder of medicines obtained according to the method of this invention is quite effective to form a stable water dispersion which may be injected subcutaneously, intramucousally or via a certain artery and thus one can expect an immediate effect.

The method according to the invention makes it possible to completely solve an important problem encountered in the conventional pharmacy.

Stability or water dispersibility may be estimated by measuring zeta potential of the ultrafine particles of medicines dispersed in water. This may, for example, be effected by using an apparatus based on laser scattering technique (for example, Zeta Sizer Type II manufactured and sold by Malvern Corporation). The ultrafine particles prepared according to the method of this invention have the zeta potential of the order of −20 mV or higher which can be considered to be reasonable and sufficient to conlude that the particles are assumed to be stably dispersed in water.

The stability of ultrafine particles dispersed in water can also be confirmed by the visual observation of the resulting water dispersion thereof, which can be prepared by introducing the resulting deposits on, for example, aluminum foil sheet cut into pieces into a tube filled with water and applying ultrasonic waves to the tube. The stability of the particles is observed after a suitable lapse of time (for example, 3 months).

While if the method according to the present invention is applied to organic compounds, the resulting ultrafine particles thereof may provide quite new uses therefor such as materials for organic sensors, catalysts, organic semiconductors, adsorbents selective to a certain material. According to the method of this invention, ultlrafine particles having a sharp size distribution may be obtained and therefore properties thereof may also become sharp enough to use the particle for a certain purpose such as pH sensor. This permits the preparation of uniform powder mixture, when the ultrafine powder is used in a mixture.

Finally, the method may also be applied to form ultrafine powder of polymers which have a quite narrow and sharp particle size distribution. However, it is well known that, according to a conventional method such as mechanical pulverization, the particle size of the resulting powder has a quite broad distribution.

The ultrafine particles obtained according to the method of this invention seem to be industrially favorable because of the use of rather simple apparatus and procedures and seem to be hardly contaminated by impurities. Therefore, the method of this invention may be an effective tool for, in particular, manufactring ultrafine particles of fine chemicals.

The method of this invention further permits the purification of the starting organic materials. In general, the purification of an objective compound may be carried out by distilling the raw material containing an objective compound, depending on the difference between boiling points of the constituents in the so-called distillation technique. In this method, the raw material is heated at a certain temperature to melt and evaporate the same and then recrystallized by cooling it and as a result the material is again purified at this stage. This fact will be evidenced by referring to the example given below, in which impurities having a boiling temperature higher than that of the objective compound remain in the container as the residue even after the completion of the procedures for preparing ultrafine particles. In other words, the impurities present in the objective compound, which is once purified before use, are removed during the procedures for evaporating and condensing the compound, once again. For example, the content of impurities in the ultrafine powder of CuCl (copper (I) chloride:semiconductor) was determined utilizing a fluorescence X-ray spectrometer, in which the ultrafine powder was prepared under the pressure of 0.1 Torr (Ar gas) and at a temperature of 450° C. (the starting material). The particle size of the resulting powder was 500 Å. Thus, the content of impurities such as Fe; Ni was significantly reduced to an order of several percent compared with those of the starting material.

The method according to the present invention will now be explained in more detail with reference to the practical illustrative examples given below.

EXAMPLE 1

Using an apparatus shown in FIG. 1, ultrafine particles of pyrene, anthracene, copper phthalocyanine, ferrocene, merocyanine and carbazole were prepared. 0.5 g of each sample was introduced in a container 6 of heating means 2, a vacuum vessel 1 was evacuated by an evacuating system 4 to a high vacuum and then Ar gas was introduced to the vessel 1 so that a desired pressure was established in the vessel 1.

While each sample was maintained at a temperature of 30° C. higher than the boiling point thereof. The recovering means 3 used herein comprises a copper plate 9 covered with aluminum foil sheet 10 and cooling pipes 11 supplied with water, which was in contact with the copper plate 9 and the temperature thereof was maintained at 25° C.

Figure 2:
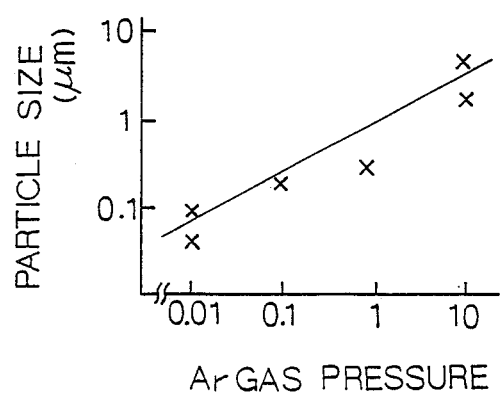
FIG. 2 is a graph showing the relationship between the mean diameter of ultrafine particles of pyrene and argon (Ar) gas pressure applied during the production procedure.

(i) Relationship between Particle Size and Pressure:

The ultrafine powder deposited on the aluminum foil sheet was examined in their particle size by an optical microscope (fluorescence microscope) and an transmission electron microscope. An example of the result obtained (pyrene) was plotted on accompanying drawing (FIG. 2) as a function of Ar pressure. As seen from the result shown in FIG. 2, the relationship between the particle size and the Ar pressure is almost linear and it was found that the particle size decreases as the pressure decreases. This tendency was also observed on all other samples.

(ii) Affinity to Water:

The aluminum foil sheet on which ultrafine particles were deposited was cut into small pieces (1 cm × 5 cm) and they were charged into a test tube filled with distilled water. Then, ultrasonic vibration was applied to the tube to disperse the powder into water. Thus, it was observed that the ultrafine particles had a good dispersibility to water and that the dispersion was in its stable state even after the lapse of 3 months.

On the other hand, fine particles of pyrene and anthracene obtained according to a conventional method (mechanical pulverization) were never dispersed in water even when a quite strong ultrasonic wave was applied.

Figure 3:
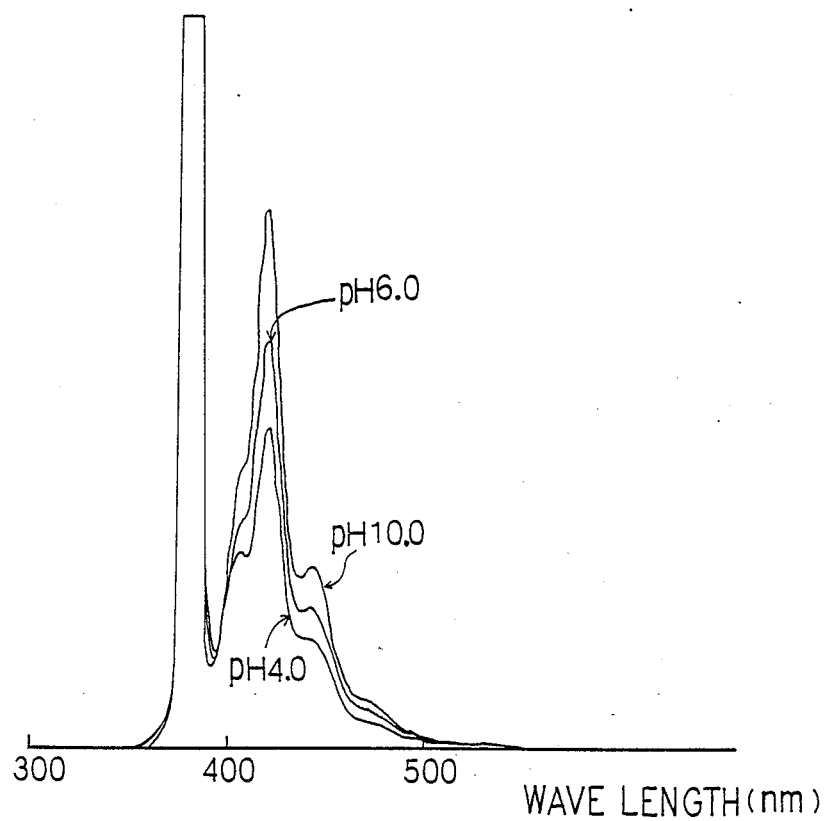
FIG. 3 is a graph in which pH dependency of the fluorescence emission spectrums observed on the ultrafine powder of anthracene is illustrated.

(iii) Optical Properties:

The ultrafine powder of pyrene and anthracene, which were both fluorescent materials, were examined on their optical properties according to fluorimetry and found that the intensity of spectral band varies depending on pH of the dispersion. The maximum fluorescence band intensity appears at the wave lengths of 370 nm (excitation spectrum) and 470 nm (emision spectrum) for pyrene, and 380 nm (excitation spectrum) and 420 nm (emission spectrum) for anthracene. These maximum band intensity were significantly reduced with the decrease in pH as seen from FIG. 3 (for anthracene). When pH was adjusted within the range of from 4 to 10, the intensity of emission spectrum is reduced to about 30% (anthracene) and to about 60% (pyrene) of the maximum value (at pH 10). The pH of the dispersion was adjusted by the addition of HCl solution, KOH solution or the mixture of HCl and HEPES buffer (pH=6.0) and the fluorescence measurement was effected by exciting the particle with irradiation of light (λ=380 nm).

This fact clearly shows that the ultrafine powder of pyrene and anthracene may be used as the material for pH sensor.

EXAMPLE 2

According to the same procedures as in the example 1, ultrafine particles of the high molecular weight compound given below were prepared:

Polyethylene ($\overline{M}_w$=93,300);
Polymethylmethacrylate ($\overline{M}_w$=96,000);
Polyvinylchloride ($\overline{M}_w$=93,000);
Polyvinylalcohol ($\overline{M}_w$=133,000);
Polystylene ($\overline{M}_w$=20,000);
Polyvinylpyrrolidone ($\overline{M}_w$=40,000);
Polyvinylcarbazole ($\overline{M}_w$=40,000);
Polyethyleneterephthalate ($\overline{M}_w$=120,000);
Polyvinylidenechloride ($\overline{M}_w$=33,000)

(i) Particle Size Distribution:

The particle size distribution was determined on ultrafine powder of each sample and found that these samples have a quite narrow and sharp size distribution which permits the uniform mixing procedure of the polymer material with other material. The water dispersibility is, of course, improved and provides a stable dispersion.

Figure 4:
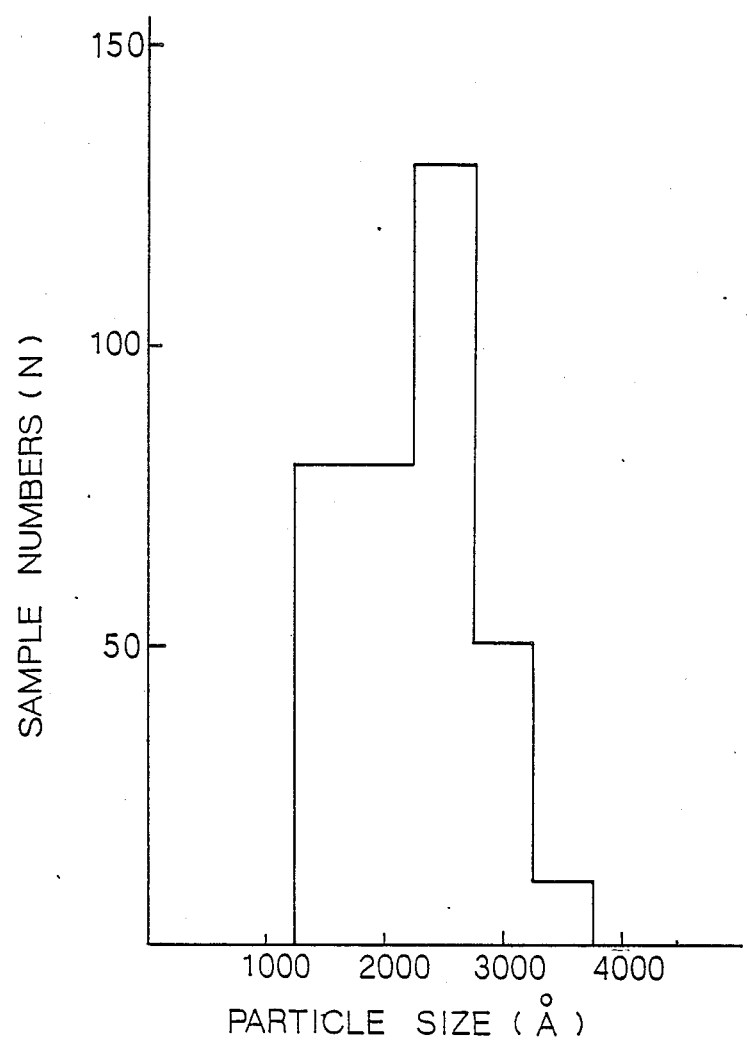
FIG. 4 is a bar graph showing particle size distribution of polymethylmethacrylate prepared (at 350° C., Ar pressure of 0.5 torr) according to the process of this invention.

An example of the result of particle size distribution measurement was shown in FIG. 4 as bar diagram (in the case of polymethylmethacrylate: $\overline{M}_w$=96,000) in which the sample number (N: ordinate) was plotted against the particle size (Å: abscissa). This result clearly shows that the ultrafine particles obtained according to the present invention exhibit very narrow and sharp size distribution (mean diameter-2,300±540 Å at 350° C., Ar pressure of 0.5 Torr). The measurement of the size distribution was carried out using transmission electron microscope.

EXAMPLE 3

The procedures disclosed in the example 1 were repeated except that the Ar pressure was adjusted to 1.0 Torr and that the following medicines were used instead of simple organic materials, as the starting material. Each starting material was heated to a temperature of 30° C. higher than the boiling point thereof, while the temperature was gradually increased in the case where clear melting point of the sample was not known.

α-bromoisovaleroylurea (III). m.p. 151°-155° C.; (sedative, hypnotic; white crystalline powder).

Barbital. m.p. 189°-192° C.; (hypnotic; crystalline powder).

Phenobarbital. m.p. 174°-178° C.; (sedative, hypnotic, antiepileptic; crystalline powder).

Phenobarbital Sodium (hypnotic, crystalline powder).

Phenytoin m.p. 296° C.; (antiepileptic; crystalline powder).

Carbamazepine. m.p. 189°-193° C.; (antiepileptic; powder).

Haloperidol. m.p. 149°-153° C.; (antimaniacal, antischizophrenic; crystalline powder).

Diazepam. m.p. 130°-134° C.; (psychotropic agent; crystalline powder).

Chlormezanone. m.p. 112°-118° C.; (minor tranquilizer; crystalline powder).

Phenacetin m.p. 134°-136° C.; (antipyretic analgesic; cyrstalline powder).

Acetaminophene. m.p. 211°-218° C; (antipyretic analgesic; crystalline powder).

Aspirin. m.p. 135° C.; (antipyretic analgesic; needle).

Ethenzamide, m.p. 131°-134° C.; (antipyretic analgesic; crystalline powder).

Phenylbutazone, m.p. 104°-107° C.; (non-steroid anti-inflammatory; crystalline powder).

Indomethacin. m.p. 155°-162° C.; (non-steroid anti-inflammatory, crystalline powder).

Mepirizole. m.p. 88°-91° C.; (non-steroid anti-inflammatory; crystalline powder).

Probenecid. m.p. 198°-200° C.; (non-steroid anti-inflammatory; crystalline powder).

Lidocaine. m.p. 66°-69° C.; (local anesthetic; white crystal).

Epinephrine (Adrenaline). m.p. 210° C.; (sympathomimetic agent; crystalline powder).

Cyproheptadine Hydrochloride. m.p. 111°–115° C.; (antihistamine; crystalline powder).

Digitoxin. (Cardiac glycoside; crystalline powder).

Sulfamonomethoxine. m.p. 204°–206° C.; (antibacterial agent; crystalline powder).

Tolubutamide. m.p. 126°–132° C.; (oral antidiabetic; crystalline powder).

Chloramphenicol. m.p. 151°–152° C.; (antibiotic; needle).

Ethyl p-hydroxybenzoate. m.p. 116°–118° C.; (disinfectant; fine crystal).

Vitamin $B_{13}$. m.p. 345°–346° C.; (colorless crystal).

Cortisone Acetate. (adrenocorticosteroid; white crystal).

Predonisone. (adrenocorticosteroid).

The medicines, vitamin and hormones used in the example are all water-insoluble or hardly soluble in water. Therefore, the development of methods for preparing a stable dispersion has been required. However, it was found that the ultrafine powder of them obtain above exhibits a good dispersibiliy in water and provides a quite stable water dispersion (suspension). This was surely be demonstrated by the dispersion test. The resulting dispersion exhibits a high stability such that the dispersed state thereof remains unchanged even after the lapse of 3 months. This fact was also evidenced by observing Zeta ($\zeta$) potential of the particles dispersed in water. The potential measurement was carried out using Zeta Sizer II (Malvern). As a result, Zeta potential was $-33.6$ mV for barbital ultrafine particles and $-22.4$ mV for indomethacin ultrafine particles in distilled water. Zeta potential of other particles is at least $-20$ mV or higher which is reasonable to conclude that the ultrafine powder of these medicines can be in the stable dispersed state such a long period of time.

What is claimed is:

1. A method for preparing ultrafine particles of an organic compound having a good affinity to a dispersion medium comprising the steps of:
    a. heating and evaporating the organic compound in a vacuum vessel while controlling the inert gas pressure in the vessel;
    b. condensing the resulting vapour and depositing on a recovering plate in the vessel; and
    wherein the inert gas is argon or nitrogen and the pressure thereof is controlled to be at highest 10 Torr.

2. A method for preparing ultrafine particles of an organic compound according to claim 1 wherein the organic compound is a member selected from the group consisting of water-insoluble or hardly water-soluble medicines, vitamins and hormones.

3. A method for preparing ultrafine particles of an organic compound according to claim 1 wherein the organic compound is a member selected from the group consisting of $\alpha$-bromoisovaleroylurea, barbital, phenobarbital, phenobarbital sodium, phenytoin, carbamazepine, haloperidol, diazepam, chlormezanone, phenacetin, acetaminophene, aspirin, ethenzamide, phenylbutazone, indomethacin, mepirizole, probenecid, lidocaine, epinephrine, cyproheptadine hydrochloride, digitoxin, sulfamonomethoxine, tolubutamide, chloramphenicol, ethyl p-hydroxybenzoate, vitamin $B_{13}$, cortisone acetate and predonisone.

4. A method for preparing ultrafine particles of an organic compound according to claim 1 wherein the organic compound is a member selected from the group consisting of anthracene, pyrene, metal phthalocyanine, merocyanine, ferrocene and carbazole.

5. A method for preparing ultrafine particles of an organic compound according to claim 1 wherein the organic compound is a member selected from the group consisting of polyvinyl chloride, polyvinylalcohol, polyethylene, polystyrene, polyvinylpyrrolidone, polyvinylcarbazole, polyethyleneterephthalate, polyvinylidenechloride and polymethylmethacrylate.

* * * * *

UNITED STATES PATENT AND TRADEMARK OFFICE
CERTIFICATE OF CORRECTION

PATENT NO. : 4,913,865
DATED : April 3, 1990
INVENTOR(S) : Hideki Toyotama

It is certified that error appears in the above-identified patent and that said Letters Patent is hereby corrected as shown below:

Column 10, Claim 3, line 18, "claim 1" should be --claim 2--.

Signed and Sealed this

Ninth Day of July, 1991

Attest:

HARRY F. MANBECK, JR.

*Attesting Officer*     *Commissioner of Patents and Trademarks*